US009074966B2

(12) United States Patent
Sanderlin et al.

(10) Patent No.: US 9,074,966 B2
(45) Date of Patent: Jul. 7, 2015

(54) SPRING FORCE NODAL MOUNTING METHOD FOR RESONATOR SENSOR

(75) Inventors: Kerry L. Sanderlin, Houston, TX (US); Yi Liu, Houston, TX (US); Rocco DiFoggio, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 416 days.

(21) Appl. No.: 13/456,811

(22) Filed: Apr. 26, 2012

(65) Prior Publication Data

US 2012/0272727 A1 Nov. 1, 2012

Related U.S. Application Data

(60) Provisional application No. 61/479,654, filed on Apr. 27, 2011.

(51) Int. Cl.
G01N 9/00 (2006.01)
G01N 11/16 (2006.01)
E21B 49/10 (2006.01)

(52) U.S. Cl.
CPC ............... G01N 9/002 (2013.01); G01N 11/16 (2013.01); E21B 49/10 (2013.01)

(58) Field of Classification Search
CPC ......... G01N 9/002; G01N 11/16; E21B 49/10
USPC .................. 73/54.24, 54.41, 152.01, 152.05, 73/152.32, 152.54, 152.11, 152.16, 73/152.17, 152.28, 152.18; 310/354
See application file for complete search history.

(56) References Cited

U.S. PATENT DOCUMENTS

| 3,139,544 | A | * | 6/1964 | Tomes ............................ 310/26 |
| 3,453,458 | A | * | 7/1969 | Smith et al. .................... 310/344 |
| 4,562,375 | A | * | 12/1985 | Besson et al. ................. 310/338 |
| 5,272,922 | A | | 12/1993 | Watson |
| 5,471,882 | A | * | 12/1995 | Wiggins ......................... 73/702 |
| 6,598,481 | B1 | * | 7/2003 | Schultz .......................... 73/702 |
| 6,938,470 | B2 | | 9/2005 | DiFoggio et al. |
| 7,162,918 | B2 | | 1/2007 | DiFoggio et al. |
| 7,207,211 | B2 | * | 4/2007 | Carlson et al. ............... 73/54.41 |
| 7,317,989 | B2 | | 1/2008 | DiFoggio et al. |
| 7,421,892 | B2 | | 9/2008 | DiFoggio et al. |
| 7,647,965 | B2 | | 1/2010 | Powell et al. |
| 7,694,734 | B2 | | 4/2010 | DiFoggio et al. |
| 7,844,401 | B2 | | 11/2010 | Reittinger |
| 2007/0113639 | A1 | * | 5/2007 | DiFoggio et al. .......... 73/152.58 |
| 2009/0120169 | A1 | * | 5/2009 | Chandler et al. ............. 73/54.41 |
| 2010/0236776 | A1 | * | 9/2010 | Spross et al. ............. 166/250.02 |

FOREIGN PATENT DOCUMENTS

EP       0211112 A1    2/1987

* cited by examiner

*Primary Examiner* — Hezron E Williams
*Assistant Examiner* — Marrit Eyassu
(74) *Attorney, Agent, or Firm* — Mossman, Kumar & Tyler, PC

(57) ABSTRACT

A resonator in the fluid for displacing the fluid has a sensing section and a non-sensing section. A compression contact member coupled to the mounting body compressively secures the resonator non-sensing section in a mounting body. The apparatus may further include a pressure feed through module received in the mounting body that is in signal communication with the resonator.

14 Claims, 3 Drawing Sheets

SPRING FORCE NODAL MOUNTING METHOD FOR RESONATOR SENSOR

CROSS-REFERENCE TO RELATED APPLICATIONS

This application claims priority from U.S. Provisional Application Ser. No. 61/479,654, filed Apr. 27, 2011, the disclosure of which is incorporated herein by reference in its entirety.

FIELD OF THE DISCLOSURE

In certain aspects, this disclosure relates to the field of fluid analysis in hydrocarbon producing wells. Also, in certain aspects, the disclosure relates to a method and apparatus for determining fluid density, viscosity, and other parameters using a flexural mechanical resonator downhole in a borehole.

BACKGROUND OF THE DISCLOSURE

Commercial development of hydrocarbon fields requires significant amounts of capital. Before field development begins, operators desire to have as much data as possible in order to evaluate the reservoir for commercial viability. While data acquisition during drilling provides useful information, it is often also desirable to conduct further testing of the hydrocarbon reservoirs in order to obtain additional data. Fluid samples extracted downhole may take weeks or longer to analyze in a surface laboratory. Thus, there is a need for a real-time downhole method and apparatus for detection, distinction and quantification of gases in the formation. However, the borehole environment can be harsh and impose considerable stresses on testing equipment.

In one aspect, the present disclosure addresses the need for test equipment that can withstand operation in a borehole.

SUMMARY OF THE DISCLOSURE

In aspects, the present disclosure provides an apparatus for determining a property of a fluid. The apparatus may include a resonator in the fluid for displacing the fluid. The resonator may have a sensing section and a non-sensing section. At least a portion of the resonator non-sensing section is disposed in a mounting body. A compression contact member coupled to the mounting body compressively secures the resonator non-sensing section in the mounting body. Preferably, this compression contact member makes its contact along a nodal line or nodal point of the resonator so as to minimize any damping of the resonator. The apparatus may further include a pressure feed through module received in the mounting body that is in signal communication with the resonator.

Examples of certain features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

In aspects, the present disclosure relates to devices and methods for providing robust mechanical and signal connections to resonators configured to characterize fluids. The teachings may be advantageously applied to a variety of systems in the oil and gas industry, water wells, geothermal wells, surface applications and elsewhere.

Figure 1:
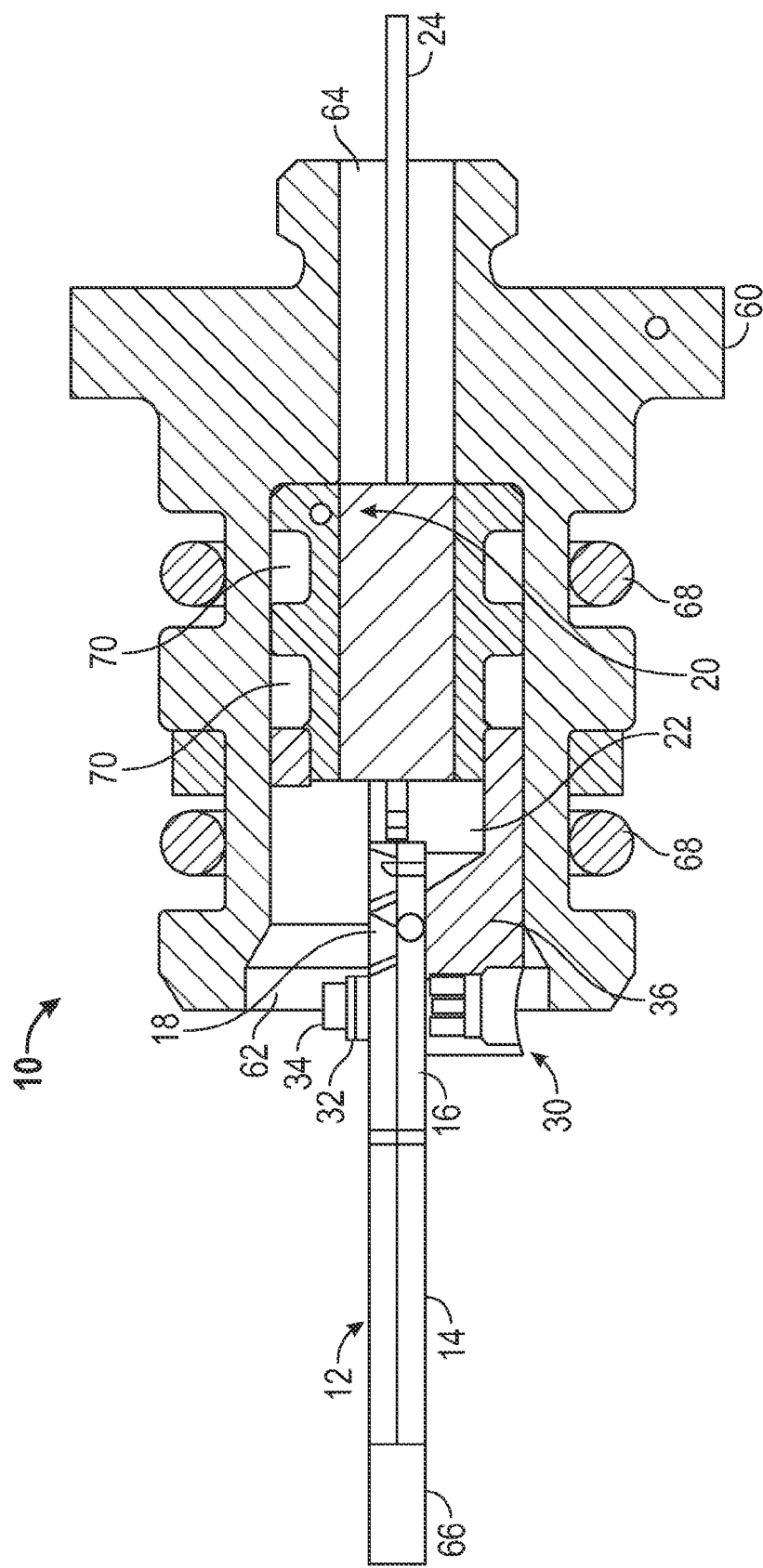
FIG. 1 sectionally illustrates an apparatus for a fluid characterization according to one embodiment of the present disclosure.

Referring to FIG. 1, there is shown a sensor assembly 10 that uses a resonator 12 to estimate one or more parameters of interest relating to downhole fluid. A resonator 12 is a device used to either generate waves of specific frequencies, which may be a resonant frequency. The resonator 12 may be a flexural mechanical resonator. Illustrative resonators include, but are not limited to, acoustical resonators, piezoelectric tuning forks and other bodies that vibrate in response to an applied excitation signal. The resonator 12 may include a sensing section 14 that is surrounded by a test fluid and a non-sensing section 16 at which electrical and mechanical connections may be made. In embodiments wherein a tuning fork shape resonator is used, the tines may be considered the sensing section 14 and the stem may be considered the non-sensing section 16.

Embodiments of the present disclosure provide the primary mechanical support of the resonator, which is in addition to any mechanical support that is provided by the electrical connection. By 'primary,' it is meant a majority or most of the support. By relieving the electrical connection of bearing a majority of the mechanical support, we significantly reduce the likelihood of resonator detachment and we also reduce the likelihood of degradation of the electrical connection from detrimental stresses that arise during manufacturing, handling, or use. In one embodiment, the resonator 12 may be in signal communication with a controller (not shown) via a pressure feed through module 20. The pressure feed through module 20 has leads 22 that connect with the resonator 12 and lead wires 24 that connect with the controller (not shown) via a suitable signal carrier (not shown). Thus, the pressure feed through module 20 is generally a device that establishes signal communication between the resonator 12 and one or more external devices via an electrical connection member. The pressure feed through module 20 may include one or more sealing elements that form a fluid (e.g., liquid and/or gas) tight barrier between two specified regions and that can withstand a predetermined pressure differential. In some arrangements, the electrical connection member may include leads 22 that are electrically connected to cups 18 formed in non-sensing section 16 of the resonator 12 with a conductive epoxy (not shown). Thus, generally, an electrical connection member is a member specifically configured to convey signals via a physical media (e.g., by including a material that conducts electromagnetic signals). This physical media may be subject to detrimental stresses during operation. However, the electrical connection member is protected from such detrimental stresses by mechanically securing the resonator 12 in a mounting assembly 30, which is described in greater detail below.

Figure 2:
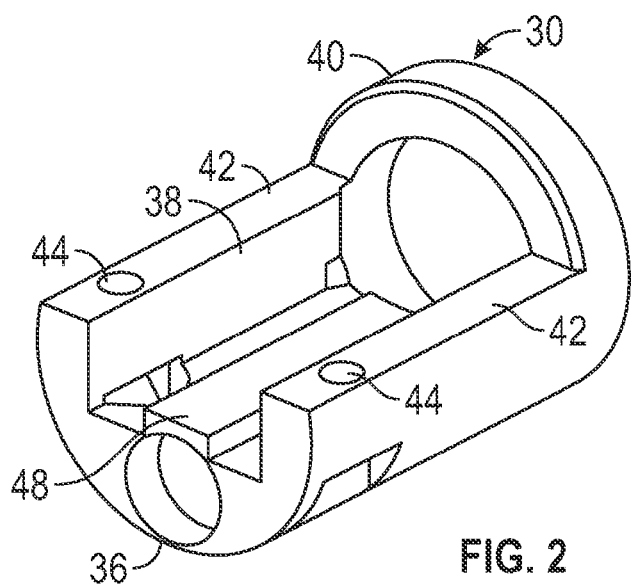
FIG. 2 isometrically illustrates a mounting body according to one embodiment of the present disclosure.

Referring still to FIG. 1, the mounting assembly 30 may be configured to provide a mechanical connection with the resonator 12 using an applied compression force. In one embodiment, the mounting assembly 30 may include a compression contact member 32, fastening elements 34, and a mounting body 36. FIG. 2 illustrates one embodiment of the mounting body 36 according to the present disclosure. The mounting body 36 may be a generally tubular member that includes an open bay 38 for receiving the resonator 12 (FIG. 1) and a ring-shaped or annular end 40 for receiving the pressure feed through lead module 20 (FIG. 1). Walls 42 defining the bay 38 may include holes 44 for receiving the fastening elements 34 (FIG. 1). The bay 38 is shaped complementary to the resonator 12 (FIG. 1) and includes a pedestal 48. The pedestal 48 is a raised portion of a surface defining the bay 38. In some embodiments, the pedestal 48 has a width that is smaller than the width of the resonator non-sensing section 16 (FIG. 1) in order to reduce undesirable effects on the motion of the resonator 12 (FIG. 1). For example, the pedestal 48 may be one-third of the width of the non-sensing section 16 (FIG. 1) and, is preferably, only in contact with the resonator along a nodal line or nodal points of the resonator so as to minimize any damping of the resonator. Simply touching the resonator with a finger or cotton swab stick can damp its resonance to the point that it can not be used as a fluid-property sensor, which is why any mechanical mounting method for the resonator must be carefully designed and implemented.

Figure 3:
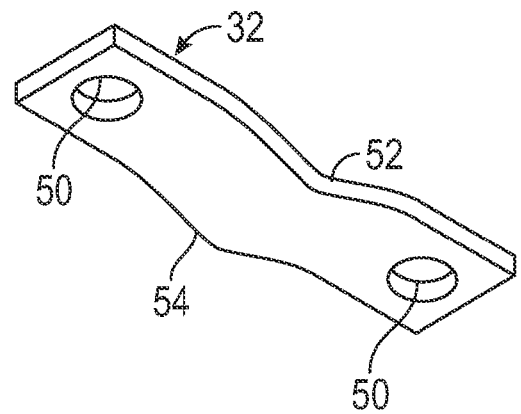
FIG. 3 isometrically illustrates a compression contact member according to one embodiment of the present disclosure.

FIG. 3 illustrates one embodiment of the compression contact member 32 that is configured to compress the resonator non-sensing section 16 (FIG. 1) against the pedestal 48 (FIG. 2). The compression contact member 32 may be a spring like member that has a sufficient modulus of elasticity to generate a spring force or it may be a magnet or magnet pair that press and hold the resonator in place on its mounting assembly. Suitable materials include, but are not limited to, spring steel and common magnets. The compression contact member 32 may include holes 50 for receiving the fastening elements 34 (FIG. 1) that fasten it to the mounting assembly. As best shown in FIG. 3, the compression contact member 32 is a generally platen member that includes a medial bend 52. The bend 52 may include an apex 54 that presents a reduced contact area between the compression contact member 32 and the resonator non-sensing section 16 (FIG. 1). While a somewhat v-shaped bend is shown, other profiles may also be suitable (e.g., arcuate, squared, etc.).

Figure 4:
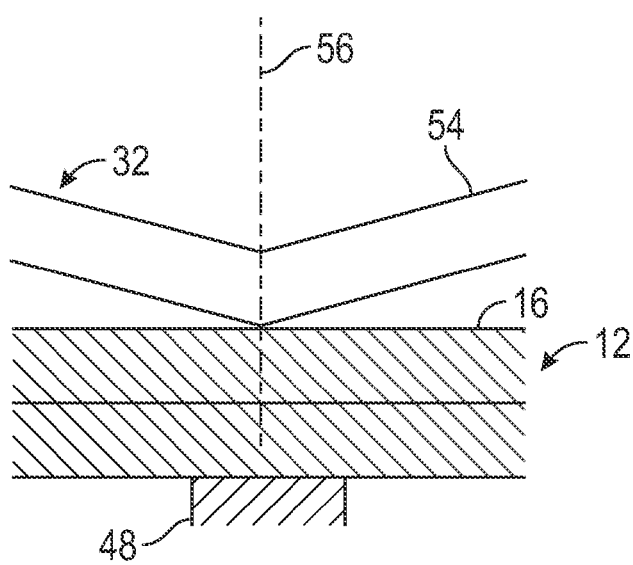
FIG. 4 sectionally illustrates a contact between a compression contact member and a resonator according to one embodiment of the present disclosure.

Referring now to FIG. 4, there is shown a sectional view of the compression contact member 32 in compressive engagement with the resonator 12. The apex 54 may contact the resonator non-sensing section 16 in a manner that minimizes the dampening effect of the applied compressive force on the operating response of the resonator 12. The apex 54 may contact the resonator non-sensing section 16 of the resonator 12 at a nodal (non-moving) line 56. In aspects, the nodal line 56 is generally defined as a line or point that remains at rest, while other parts of the body are in a state of vibration. The nodal line 56 may be a bilateral axis of symmetry. It should be understood, however, that the location and orientation of the nodal line 56 may vary depending on the shape and behavior of the resonator 12. The compressive force applied by the compression contact member 32 (FIG. 1) is the primary mechanism to secure the resonator 12. The compressive force must be sufficient to hold the resonator in place as well as relieve detrimental stresses on the electrical leads that connect between the resonator 12 and the pressure feed through lead module 20. However, the compressive force must not be so great as to initiate any cracks in a brittle resonator. The detrimental stresses on the electrical leads can arise from passing fluid and debris and from shock and vibration all of which tend to loosen the electrical-lead connection, which is made using a conductive epoxy. This electrical-lead loosening effect becomes more pronounced at high temperatures, which soften the conductive epoxy.

It should be appreciated that the compression contact member 32 is substantially separate from the electrical connection member (e.g., the leads 22 (FIG. 1) and the epoxy (not shown)) or a portion of the electrical connection member (e.g., the epoxy (not shown)). In one aspect, 'separate' generally means that each member has separate structural components that can perform its function independent of the other (e.g., secure the resonator 12 independent of conveying signals to/from the resonator 12).

Referring now to FIG. 1, the sensor assembly 10 may include a housing 60 to house the resonator 12, the mounting assembly 30, and the pressure feed through lead module 20. The housing 60 may include a cavity 62 for receiving the pressure feed through module 20 and mounting assembly 30. The housing 60 may also include a passage 64 through which the lead wires 24 may extend. To protect the resonator sensing section 14 from passing debris, a pair of pins 66 aligned with the resonator sensing section 14 may extend from the housing 60 and shield the resonator tine from such debris. Because FIG. 1 is a sectional drawing, only the outermost portion of one pin 66, which is behind the resonator sensing section 14, is shown. During operation, the resonator sensing section 14 may be immersed in a flowing liquid. The pins 66 act as guards or blocks that prevent debris or other materials in the flowing liquid from impacting the resonator sensing section 14.

Fluid seals may be used to prevent undesirable contact between the sensor assembly 10 and liquids encountered during operation. Seals 68 may be positioned on the outer surfaces of the housing 60 to provide a fluid tight seal with a surrounding structure, e.g., a formation sampling tool. Interior seals 70 may provide a fluid tight seal between the pressure feed through module 20 and the housing 60. Also, a sealant may be applied to the cavity 62 to protect the resonator 12 and pressure feed through module 20. This sealant may "wick" along the interstitial spaces in the cavity 62 to prevent conductive fluids from affecting calibration of the resonator 12 or otherwise affect operation of the resonator 12. In some embodiments, the sealant may be a liquid-repelling elastomeric gel.

Figure 5:
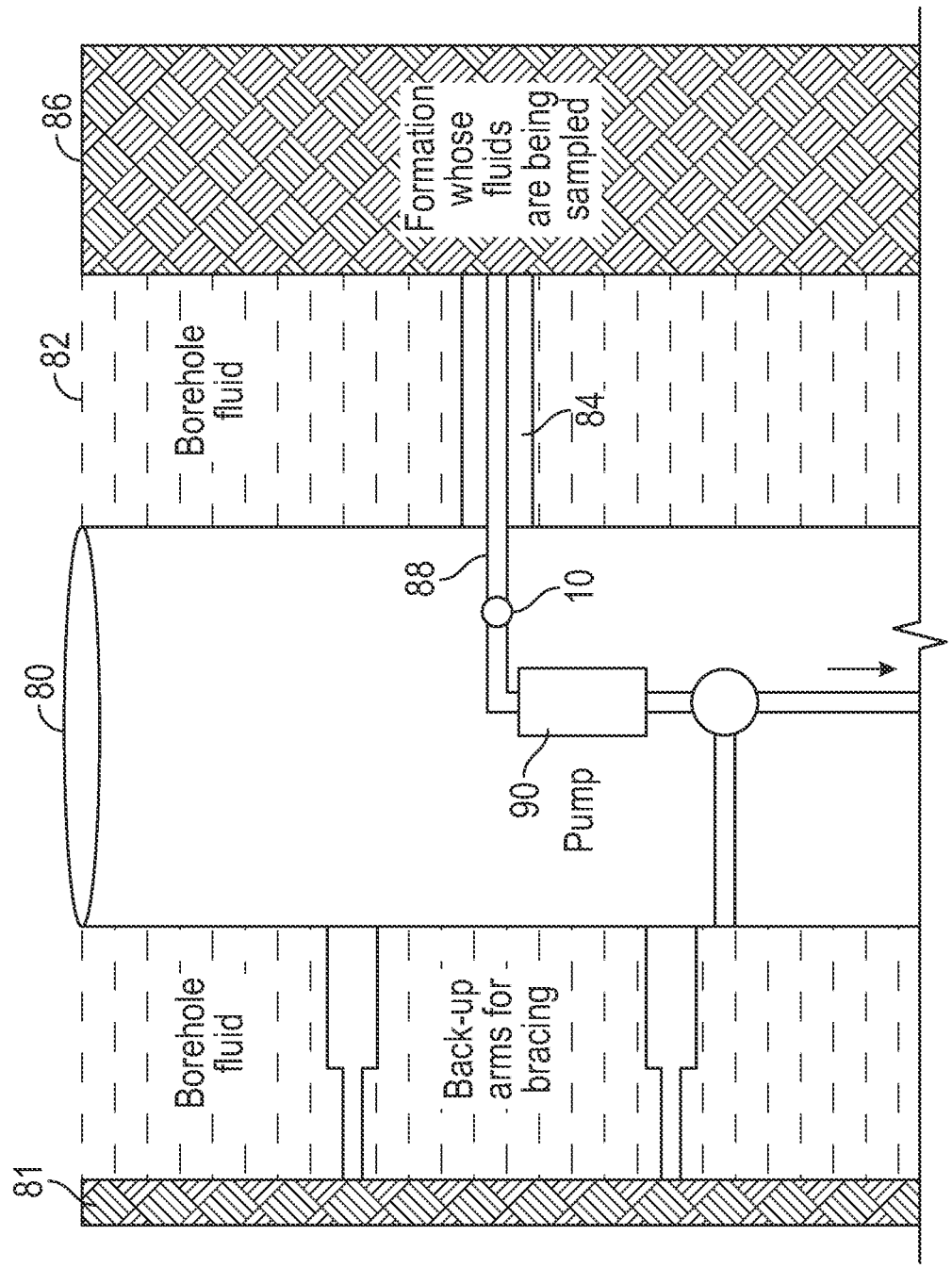
FIG. 5 shows a schematic of an apparatus for implementing one embodiment of the method according to the present disclosure.

The mechanical connections of the present disclosure may be used in a variety of surface and subsurface application. For illustrative purposes, FIG. 5 shows a fluid characterization sensor assembly 10 according to one embodiment of the present disclosure in a downhole environment. The sensor assembly 10 may be deployed via a suitable carrier 80 in a borehole 81 filled with borehole fluid 82. A probe 84 may contact a borehole wall for extracting formation fluid from the formation 86. The sensor assembly 10 may be disposed in a flowline 88. A pump 90 may draw formation fluid from formation 86 into the flowline 88. Referring now to FIGS. 1 and 5, the resonator 12, when excited, exhibits a response in the presence of a formation fluid sample that may be utilized to determine fluid density, viscosity, dielectric coefficient, and/or other properties, when the fluid is pumped by pump 90 or when the fluid is static, that is, when pump 90 is stopped.

It should be appreciated that using a mechanical connection that is functionally isolated from the electrical connection may increase the reliability and service life of the sensor assembly 10. For instance, the stresses associated with manufacturing, handling, and transportation can be primarily borne by mechanical connection formed by pinching the tuning fork non-sensing section 16 between the mounting assembly 30 and the compression contact member 32. Thus, the integrity of the electrical connections is preserved during such activities. Further, considerable stresses may be imposed on the sensor assembly 10 during deployment into the well and operation. Again, the electrical connections are protected from these stresses by the mounting assembly 20.

From the above, it should be appreciated that the present disclosure includes, in part, an apparatus for determining a property of a fluid. The apparatus may include a resonator in the fluid, the resonator having a sensing section and a non-sensing section; a mounting body in which at least a portion of the resonator non-sensing section is disposed; a pressure feed through module received in the mounting body; an electrical connection member configured to transmit signals between the pressure feed through module and the resonator; and a compression contact member coupled to the mounting body, the compression contact member compressively securing the resonator non-sensing section in the mounting body, the compression contact member being substantially separate from the electrical connection member.

From the above, it should be appreciated that the embodiments of the present disclosure include a method for determining a property of a fluid. The method many include positioning a sensor assembly in a wellbore, exciting a resonator associated with the sensor assembly with an excitation signal; and estimating a response of the resonator to the excitation signal. The sensor assembly may include a resonator having a sensing section and a non-sensing section; a mounting body in which at least a portion of the resonator non-sensing section is disposed; a pressure feed through module received in the mounting body; an electrical connection member configured to transmit signals between the pressure feed through module and the resonator; and a compression contact member coupled to the mounting body, the compression contact member compressively securing the resonator non-sensing section in the mounting body, the compression contact member being substantially separate from the electrical connection member.

The term "carrier" as used in this disclosure means any device, device component, combination of devices, media and/or member that may be used to convey, house, support or otherwise facilitate the use of another device, device component, combination of devices, media and/or member. As used herein, the term "fluid" and "fluids" refers to one or more gasses, one or more liquids, and mixtures thereof.

While the foregoing disclosure is directed to the one mode embodiments of the disclosure, various modifications will be apparent to those skilled in the art. It is intended that all variations be embraced by the foregoing disclosure.

We claim:

1. An apparatus for determining a property of a fluid, comprising:
    a resonator in the fluid, the resonator having a sensing section and a non-sensing section;
    a mounting body in which at least a portion of the resonator non-sensing section is disposed;
    a pressure feed through module received in the mounting body;
    an electrical connection member configured to transmit signals between the pressure feed through module and the resonator; and
    a compression contact member coupled to the mounting body, the compression contact member compressively securing the resonator non-sensing section in the mounting body, the compression contact member being substantially separate from the electrical connection member,
    wherein the compression contact member has a reduced contact area that contacts the resonator non-sensing section at a nodal line of the resonator non-sensing section.

2. The apparatus of claim 1, wherein the reduced contact area is at a bent portion that contacts the resonator non-sensing section.

3. The apparatus of claim 1, wherein the mounting body includes a bay having a pedestal, the resonator non-sensing section being secured only between the compression contact member and the pedestal, wherein the resonator non-sensing section has a first and a second opposing surfaces, the compression contact member being in contact with the first opposing surface and the pedestal being in contact with the second opposing surface.

4. The apparatus of claim 3, wherein the pedestal has a width smaller than a width of the resonator non-sensing section.

5. The apparatus of claim 1, wherein the compression contact member includes an apex region, and wherein only the apex region contacts the resonator non-sensing section.

6. The apparatus of claim 1, wherein the resonator is configured to estimate at least one of: (i) a fluid property, (ii) fluid density, and (iii) fluid viscosity.

7. The apparatus of claim 1, further comprising:
    a fluid sampling tool having a probe, a fluid line, and pump;
    a housing for receiving the resonator, the mounting body, and the pressure feed through module, the housing being disposed in the fluid sampling tool, wherein at least a portion of the sensing section of the resonator is in fluid communication with a fluid in the flow line; and
    a carrier configured to convey the fluid sampling tool in a borehole.

8. A method for determining a property of a fluid, comprising:
    positioning a sensor assembly in a wellbore, the sensor assembly including:
        a resonator having a sensing section and a non-sensing section;
        a mounting body in which at least a portion of the resonator non-sensing section is disposed;
        a pressure feed through module received in the mounting body;
        an electrical connection member configured to transmit signals between the pressure feed through module and the resonator; and
        a compression contact member coupled to the mounting body, the compression contact member compressively securing the resonator non-sensing section in the mounting body, the compression contact member being substantially separate from the electrical connection member;
    positioning a reduced contact area of the compression contact member to contact the resonator non-sensing section at a nodal line of the resonator non-sensing section;
    exciting the resonator with an excitation signal; and
    estimating a response of the resonator to the excitation signal.

9. The method of claim 8, further comprising estimating a fluid property using the estimated response of the resonator.

10. The method of claim 9 wherein the fluid property is one of: (i) fluid density, and (ii) fluid viscosity.

11. The method of claim 8, further comprising:
retrieving the fluid from a formation using a probe, a fluid line, and pump.

12. The method of claim 8, further comprising:
positioning at least a portion of the sensing section of the resonator in fluid communication with a fluid in the flow line.

13. The method of claim 8, further comprising:
conveying the sensor assembly into the wellbore using a carrier.

14. An apparatus for determining a property of a fluid, comprising:
- a resonator in the fluid, the resonator having a sensing section and a non-sensing section, the resonator having a nodal line that remains at rest while other parts of the resonator are in a state of vibration;
- a mounting body in which at least a portion of the resonator non-sensing section is disposed;
- a pressure feed through module received in the mounting body;
- an electrical connection member configured to transmit signals between the pressure feed through module and the resonator; and
- a compression contact member coupled to the mounting body and having a reduced contact area, the compression contact member compressively securing the resonator non-sensing section in the mounting body, wherein the reduced contact area contacts the nodal line of the resonator non-sensing section.

\* \* \* \* \*